United States Patent
Draper et al.

(10) Patent No.: US 10,596,326 B2
(45) Date of Patent: *Mar. 24, 2020

(54) DRUG INJECTION DEVICE WITH RESETTABLE MECHANISM ALLOWING PISTON ROD RETRACTION UPON DRUG CARTRIDGE CHANGE

(71) Applicant: Sanofi, Paris (FR)

(72) Inventors: Paul Richard Draper, Evesham (GB); Joseph Butler, Rugby (GB)

(73) Assignee: Sanofi, Paris (FR)

( * ) Notice: Subject to any disclaimer, the term of this patent is extended or adjusted under 35 U.S.C. 154(b) by 239 days.

This patent is subject to a terminal disclaimer.

(21) Appl. No.: 15/517,863

(22) PCT Filed: Oct. 9, 2015

(86) PCT No.: PCT/EP2015/073432
§ 371 (c)(1),
(2) Date: Apr. 7, 2017

(87) PCT Pub. No.: WO2016/055627
PCT Pub. Date: Apr. 14, 2016

(65) Prior Publication Data
US 2017/0312441 A1    Nov. 2, 2017

(30) Foreign Application Priority Data
Oct. 9, 2014  (EP) ..................... 14306594

(51) Int. Cl.
*A61M 5/315*    (2006.01)
*A61M 5/20*    (2006.01)
(Continued)

(52) U.S. Cl.
CPC .......... *A61M 5/31551* (2013.01); *A61M 5/20* (2013.01); *A61M 5/24* (2013.01);
(Continued)

(58) Field of Classification Search
CPC .......... A61M 5/31551; A61M 5/31541; A61M 5/31543; A61M 5/31583; A61M 5/31591
See application file for complete search history.

(56) References Cited

U.S. PATENT DOCUMENTS 5,104,380 A * 4/1992 Holman ................. A61M 5/20
604/117
2003/0050609 A1    3/2003 Sams
(Continued)

FOREIGN PATENT DOCUMENTS

CN  103167890  6/2013
WO  WO 02/092153  11/2002
(Continued)

OTHER PUBLICATIONS

International Preliminary Report on Patentability in International Application No. PCT/EP2015/073432, dated Apr. 11, 2017, 8 pages.
(Continued)

*Primary Examiner* — Nathan R Price
*Assistant Examiner* — John A Doubrava
(74) *Attorney, Agent, or Firm* — Fish & Richardson P.C.

(57) ABSTRACT

A drug delivery device for selecting and dispensing a number of user variable doses of a medicament. The device comprises a housing, a dose setting element rotatable relative to the housing during dose setting and dose dispensing, a drive member coupled to the dose setting member via a clutch, and a piston rod coupled to the housing and to the drive member Further, the device further comprises a cartridge holder removably attached to the housing and a reset element, which is permanently rotationally constrained to the housing and rotationally constrained to the drive member during dose setting, and at least one spring acting on the reset element, such that, if the cartridge holder is detached from the housing, the reset element is axially moved relative to the housing into a position in which the drive member is allowed to rotate relative to the housing.

19 Claims, 5 Drawing Sheets

(51) Int. Cl.
*A61M 5/24* (2006.01)
*A61M 5/31* (2006.01)

(52) U.S. Cl.
CPC .... *A61M 5/31541* (2013.01); *A61M 5/31543* (2013.01); *A61M 5/31585* (2013.01); *A61M 5/31591* (2013.01); *A61M 5/31553* (2013.01); *A61M 5/31593* (2013.01); *A61M 2005/202* (2013.01); *A61M 2005/2407* (2013.01); *A61M 2005/2477* (2013.01); *A61M 2005/3126* (2013.01); *A61M 2005/3154* (2013.01); *A61M 2205/581* (2013.01); *A61M 2205/582* (2013.01)

(56) References Cited

U.S. PATENT DOCUMENTS

| | | | |
|---|---|---|---|
| 2009/0247960 A1 | 10/2009 | Kohlbrenner et al. | |
| 2010/0274198 A1 | 10/2010 | Bechtold | |
| 2010/0331788 A1* | 12/2010 | Plumptre | A61M 5/31543 604/207 |
| 2011/0224622 A1 | 9/2011 | Karlsson | |
| 2012/0136315 A1* | 5/2012 | Wieselblad | A61M 5/20 604/189 |
| 2012/0209212 A1* | 8/2012 | Plumptre | A61M 5/31543 604/207 |
| 2013/0096513 A1 | 4/2013 | Smith | |
| 2016/0129196 A1* | 5/2016 | Hirschel | A61M 5/31541 604/211 |
| 2016/0235924 A1* | 8/2016 | Soerensen | A61M 5/24 |
| 2017/0173268 A1* | 6/2017 | Enggaard | A61M 5/20 |

FOREIGN PATENT DOCUMENTS

| | | |
|---|---|---|
| WO | WO 2006/126902 | 11/2006 |
| WO | WO 2013/119132 | 8/2013 |

OTHER PUBLICATIONS

International Search Report and Written Opinion in International Application No. PCT/EP2015/073432, dated Dec. 10, 2015, 12 pages.

* cited by examiner

Figure 3
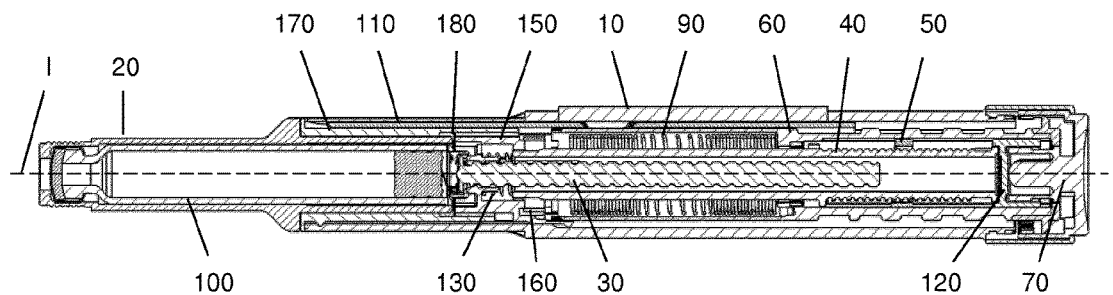
Figure 4
Figure 5
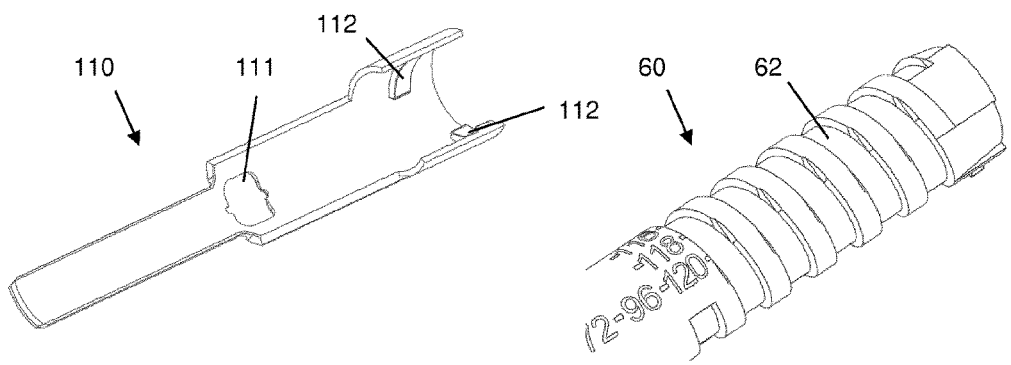
Figure 6
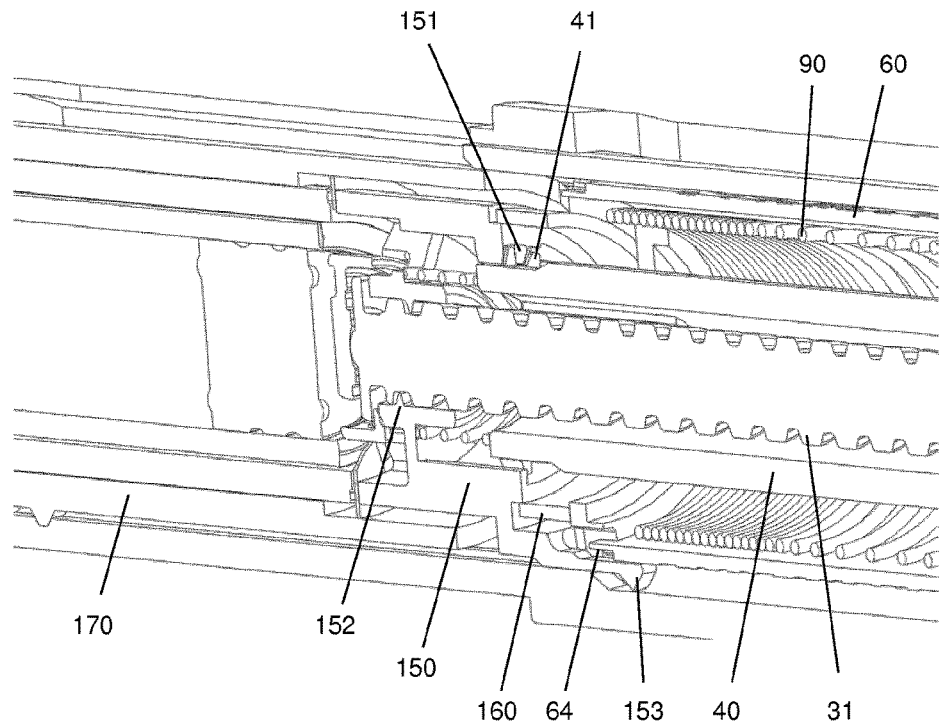

DRUG INJECTION DEVICE WITH RESETTABLE MECHANISM ALLOWING PISTON ROD RETRACTION UPON DRUG CARTRIDGE CHANGE

CROSS-REFERENCE TO RELATED APPLICATIONS

This application is a U.S. national stage application under 35 USC § 371 of International Application No. PCT/EP2015/073432, filed on Oct. 9, 2015, which claims priority to European Patent Application No. 14306594.4 filed on Oct. 9, 2014, the entire contents of which are incorporated herein by reference.

TECHNICAL FIELD

The present disclosure is generally directed to a drug delivery device for selecting and dispensing a number of user variable doses of a medicament, and a method of assembling same.

BACKGROUND

Pen type drug delivery devices have application where regular injection by persons without formal medical training occurs. This may be increasingly common among patients having diabetes where self-treatment enables such patients to conduct effective management of their disease. In practice, such a drug delivery device allows a user to individually select and dispense a number of user variable doses of a medicament. The present disclosure is not directed to so called fixed dose devices which only allow dispensing of a predefined dose without the possibility to increase or decrease the set dose.

There are basically two types of drug delivery devices: resettable devices (i.e., reusable) and non-resettable (i.e., disposable). For example, disposable pen delivery devices are supplied as self-contained devices. Such self-contained devices do not have removable pre-filled cartridges. Rather, the pre-filled cartridges may not be removed and replaced from these devices without subverting the device itself. Consequently, such disposable devices need not have a resettable dose setting mechanism. The present disclosure is directed to reusable devices which allow resetting of the device and a replacement of a cartridge. Resetting of the device typically involves moving a piston rod or lead screw from an extended (distal) position, i.e. a position after dose dispensing, into a more retracted (proximal) position.

These types of pen delivery devices (so named because they often resemble an enlarged fountain pen) generally comprise three primary elements: a cartridge section that includes a cartridge often contained within a housing or holder; a needle assembly connected to one end of the cartridge section; and a dosing section connected to the other end of the cartridge section. A cartridge (often referred to as an ampoule) typically includes a reservoir that is filled with a medication (e.g., insulin), a movable rubber type bung or stopper located at one end of the cartridge reservoir, and a top having a pierceable rubber seal located at the other, often necked-down, end. A crimped annular metal band is typically used to hold the rubber seal in place. While the cartridge housing may be typically made of plastic, cartridge reservoirs have historically been made of glass.

The needle assembly is typically a replaceable double-ended needle assembly. Before an injection, a replaceable double-ended needle assembly is attached to one end of the cartridge assembly, a dose is set, and then the set dose is administered. Such removable needle assemblies may be threaded onto, or pushed (i.e., snapped) onto the pierceable seal end of the cartridge assembly.

The dosing section or dose setting mechanism is typically the portion of the pen device that is used to set (select) a dose. During an injection, a spindle or piston rod contained within the dose setting mechanism presses against the bung or stopper of the cartridge. This force causes the medication contained within the cartridge to be injected through an attached needle assembly. After an injection, as generally recommended by most drug delivery device and/or needle assembly manufacturers and suppliers, the needle assembly is removed and discarded.

A further differentiation of drug delivery device types refers to the drive mechanism: There are devices which are manually driven, e.g. by a user applying a force to an injection button, devices which are driven by a spring or the like and devices which combine these two concepts, i.e. spring assisted devices which still require a user to exert an injection force. The spring-type devices involve springs which are preloaded and springs which are loaded by the user during dose selecting. Some stored-energy devices use a combination of spring preload and additional energy provided by the user, for example during dose setting.

SUMMARY

Manually driven reusable drug delivery devices are known e.g. from WO 2014/033195 A1 and EP 2 274 030 B1. These devices comprise a last dose mechanism preventing setting of a dose which exceeds the amount of medicament remaining in the cartridge. Replacing a cartridge allows resetting of this last dose mechanism by pushing the piston rod in a direction opposite to the dispensing direction.

Further, EP 1 819 382 B1 discloses a spring driven drug delivery device with a housing, a dose setting element rotatable relative to the housing during dose setting and dose dispensing between a minimum dose position and a maximum dose position, a drive member coupled to the dose setting member via a ratchet, and a piston rod threaded to a housing insert and rotationally constrained to the drive member. Resetting of the device is mentioned in this document differing from the above definition as the process of reducing a set dose. Replacing a cartridge and resetting e.g. the piston rod is not disclosed in EP 1 819 382 B1.

Some aspects of the disclosure may be implemented to provide an improved resettable drug delivery device.

A drug delivery device according to the present disclosure is suitable for selecting and dispensing a number of user variable doses of a medicament. The device typically comprises a housing, a dose setting element, a drive member coupled to the dose setting member via a clutch and a piston rod coupled to the housing and to the drive member. Preferably, the dose setting member is rotatable relative to the housing during dose setting, i.e. increasing or decreasing the dose, and dose dispensing between a minimum dose position and a maximum dose position. The drive member may be rotationally coupled to the dose setting member via a slipping clutch during dose setting and rotationally constrained to the dose setting member during dose dispensing. The present disclosure is based on the idea of providing a cartridge holder removably attached to the housing and a reset element. The reset element is preferably permanently rotationally constrained to the housing and rotationally constrained to the drive member at least, and preferably only, during dose setting. The reset element is rotationally constrained to the housing. This allows the reset element to rotationally constrain or unconstrain component parts to the housing by engaging or disengaging the reset element with component parts. The axial movement of the reset element between the resetting mode and the dose setting and dose dispensing mode may thus be used to couple or decouple component parts to or from the housing. Further at least one spring may be provided acting on the reset element, such that, upon detaching the cartridge holder from the housing, the reset element is axially moved relative to the housing into a position in which the drive member is allowed to rotate relative to the housing. In the resetting condition of the device, i.e. with the cartridge holder removed from the housing, the at least one spring holds the reset element in the resetting position, preferably a distal position, in which the drive member is allowed to spin free relative to the housing. In other words, detachment of the cartridge holder from the housing allows an axial movement of the reset element into a resetting position, in which the drive member may be rotated relative to the housing and preferably also relative to the dose setting member. As the piston rod is coupled to the housing and to the drive member, e.g. via a threaded interface with the housing or a housing insert, e.g. a reset element, and a splined interface with the drive member, resetting of the piston rod requires free rotation of the drive member. Thus, resetting of the drug delivery device may be performed simply by pushing back the piston rod or lead screw after removal of the cartridge holder.

During re-attachment of the cartridge holder to the housing the cartridge holder moves the reset element against the bias of the at least one spring into a dose setting and dose dispensing position in which the drive member is releasably rotationally constrained to the housing. If the cartridge holder is fully attached to the housing, the cartridge holder holds the reset element against the bias of the at least one spring in the dose setting and dose dispensing position. Thus, attachment of the cartridge holder locks the device in a dose setting and dose dispensing mode allowing dose setting and dose dispensing.

The reset element preferably comprises clutch teeth and the drive member comprises corresponding clutch teeth for releasably rotationally constraining the drive element to the reset element depending on the relative axial position of the reset element and the drive member. In a preferred embodiment, it is the reset element which is axially moved relative to the drive member and to the housing to switch the device from a dose setting and dispensing mode to a resetting mode (and vice versa), while it is an axial movement of the drive member relative to the reset element and to the housing which switches the device between a dose setting mode with the drive member rotationally fixed to the housing and a dose dispensing mode which allows rotation of the drive member. In other words, the drive member is axially movable relative to the housing between a dose setting position in which, if the cartridge holder is attached to the housing, the drive member is rotationally constrained to the housing via the reset element and a dose dispensing position in which, if the cartridge holder is attached to the housing, the drive member is rotatable relative to the reset element and the housing. Thus, the axial position of the drive member determines whether the device is in a dose setting mode allowing a user to increase or decrease a dose by rotation of the dose setting member without dispensing medicament or in a dose dispensing mode allowing a user to dispense a set dose by rotation of the dose setting element and the drive member.

In a further development of this embodiment, the clutch between the dose setting element and the drive member is a slipping clutch with first clutch teeth on the drive member and second clutch teeth on a clutch plate, which is, preferably permanently, rotationally constrained to the dose setting element during dose setting and dose dispensing. As an alternative, the clutch plate could be made the same component as the dose setting element. For example, the first and/or second clutch teeth may each be distributed as a ring of teeth, preferably facing in the axial direction. The clutch features and the corresponding clutch features may each comprise a series of teeth, preferably saw-teeth, which are allowed to slip over each other if not pressed against each other too firmly. In other words, the clutch features may be overhauled against the axial bias of the clutch spring by allowing one or both clutch elements to translate axially against the force of the clutch spring. This may result in an oscillating axial movement of one or both clutch elements due to continued disengagement and following re-engagement into the next detented position. An audible click may be generated by this re-engagement, and tactile feedback may be given by the change in torque input required.

The at least one spring may bias the clutch features into abutment. The spring may comprise a trigger or clutch spring in the form of a helical compression spring and a reset spring in the form of a helical compression spring. As an alternative, the reset spring might be a wave spring. At their distal ends, the trigger spring and the reset spring both bear onto the thread insert (reset element). At its distal end, the trigger spring bears onto the drive sleeve. At its distal end the reset spring bears onto an inner flange feature within the housing. At reset, the trigger spring force is reduced by the distal movement of the reset element and becomes small or zero. This allows the drive sleeve to spin easily and so allows reset. At reset, the reset spring holds the reset element in a distal position despite the reset force on the piston rod. At its distal end, the drive spring also attaches to this inner flange feature within the housing.

According to a preferred embodiment, the drug delivery device is a spring driven device. A drive spring, preferably a torsion spring, may be interposed between the housing and the dose setting element. Providing a resilient drive member, such as a torsion spring, generating the force or torque required for dose dispensing reduces the user applied forces for dose dispensing. This is especially helpful for users with impaired dexterity. In addition, the dial extension of the known manually driven devices, which is a result of the required dispensing stroke, may be omitted by providing the resilient member because merely a small triggering stroke may be necessary for releasing the resilient member. The drive spring may be pre-charged, at least partly, and/or may be charged by a user during dose setting.

For spring driven devices, it may be desirable to prevent rotation of the dose setting element and the drive spring during resetting of the device. Therefore, the device preferably further comprises a clutch which is decoupled if the cartridge holder is attached to the housing and which is coupled if the cartridge holder is detached from the housing. The clutch may rotationally couple the dose setting element and the reset element. In a preferred embodiment, this clutch comprises at least one flexible arm which is guided into engagement with the dose setting element upon axial movement of the reset element into its resetting position. Moving the reset element back into the dose setting and dispensing position results in disengaging the dose setting element from the reset element and, thus, from the housing to allow rotation of the dose setting member for dose setting, dose correction and dose dispensing.

The reset element may further comprise an inner thread engaging an outer thread of the piston rod. With the reset element rotationally constrained to the housing, this results in an axial displacement of the piston rod along a helical path upon rotation of the drive member. Preferably, the drive member is rotationally constrained to the piston rod but allows relative axial movement thereto. As an alternative, the piston rod may be rotationally constrained to the reset element and in threaded engagement with the drive member.

Preferably, the clutch between the drive member and the dose setting element is a slipping clutch which allows relative rotation between the drive member and the dose setting element in both directions during dose setting for increasing or decreasing a set dose. If the device is a spring driven device, the clutch teeth may be designed to provide a different resistance for overcoming the clutch depending on the direction of the relative rotation. For example, the ramp angle may be shallower resulting in a lower resistance in the dose increasing direction and steeper resulting in a higher resistance in the dose decreasing direction.

The drug delivery device may further comprise at least one bias spring axially interposed between the cartridge and the reset element. This additional spring may compensate length tolerances of the cartridge and further bring the cartridge in a defined distal position. As an alternative, the bias spring may be omitted with the proximal rim (edge) of the cartridge directly contacting the reset element if the cartridge holder is fully attached to the housing.

In another preferred embodiment, the drug delivery device further comprises a gauge element radially interposed between the housing and the dose setting element. The gauge element is axially movable relative to the housing and in threaded engagement with the dose setting element. The housing may comprise at least one aperture and the gauge element may comprise at least one aperture. If the dose setting element is a number sleeve which comprises markings on its outer surface, at least one of the markings is visible through the aperture in the gauge element and the aperture in the housing during dose setting and dose dispensing. The term aperture may include a simple opening in the housing or gauge element or a transparent window or lens. A window in the housing may be incorporated using a 'twin-shot' moulding technology. For example, the housing is moulded during a 'first shot' in a translucent material, and the outer cover of the housing is moulded during a 'second shot' in an opaque material.

The gauge element may be axially guided within the housing such that rotation of the dose setting element causes an axial displacement of the gauge element. The position of the gauge element may thus be used to identify the actually set and/or dispensed dose. Different colours of sections of the gauge member may facilitate identifying the set and/or dispensed dose without reading numbers, symbols or the like on a display. As the gauge element is in threaded engagement with the dose setting element, rotation of the dose setting element causes an axial displacement of the gauge element relative to the dose setting element and relative to the housing. The gauge element may have the form of a shield or strip extending in the longitudinal direction of the device. As an alternative, the gauge element may be a sleeve. In an embodiment, the dose setting element is marked with a sequence of numbers or symbols arranged on a helical path. With the dose setting element located radially inwards of the gauge element, this allows that at least one of the numbers or symbols on the dose setting element is visible through the aperture or window. In other words, the gauge element may be used to shield or cover a portion of the dose setting element and to allow viewing onto only a limited portion of the dose setting element. This function may be in addition to the gauge element itself being suitable for identifying or indicating the actually set and/or dispensed dose.

In general, the concept of the gauge element and the dose setting element is applicable for various types of devices with or without a drive spring. In a preferred embodiment, the dose setting element, during dose setting, is adapted to undergo a mere rotational movement within the housing and relative to the housing. In other words, the dose setting element does not perform a translational movement during dose setting. This avoids that the dose setting element is wound out of the housing or that the housing has to be lengthened to cover the dose setting element within the housing.

The relative movements of the gauge element and the dose setting element may further be used to define the minimum dose position and the maximum dose position. Typically, the minimum settable dose is zero (0 IU of insulin formulation), such that the limiter stops the device at the end of dose dispensing. The maximum settable dose, for example 60, 80 or 120 IU of insulin formulation, may be limited to reduce the risk of overdosage and to avoid the additional spring torque needed for dispensing very high doses, while still being suitable for a wide range of patients needing different dose sizes. Preferably, the limits for the minimum dose and the maximum dose are provided by hard stop features. For example, the gauge element comprises a minimum dose rotational stop and a maximum dose rotational stop and the dose setting element comprises a minimum dose rotational counter stop and a maximum dose rotational counter stop. Abutment of the respective stop and counter stop blocks further relative movement between the gauge element and the dose setting element. As the dose indicator rotates relative to the gauge element during dose setting and during dose dispensing, these two components are suitable to form a reliable and robust limiter mechanism.

The device may further comprise a dispensing button or trigger. The button is preferably a user operable element located proximally of the drive sleeve and the clutch element. When used in a drug delivery device, the button may extend from the proximal end of the device and, preferably, does not change its axial position during dose setting. The button is preferably coupled to a user operable dose selector and may be releasably coupled to a number sleeve component and/or a stationary housing component. In an alternative embodiment, the button may be part of a dose setting arrangement or may be the dose setting member. The button may be a multi-functional element having in addition to the above features e.g. a clicker feature.

The stationary housing component is a fixed basis for relative movements of the axially movable sleeve, e.g. the drive sleeve, the clutch element and the button. It may be part of a multi-component housing or may be the only housing component of a drug delivery device. In a preferred embodiment, the housing comprises an outer housing shell and an inner housing, which are constrained to each other. The housing and inner housing fix together to provide a contiguous housing for the device. The inner housing provides support and attachment for the cartridge holder. The housings provide an inward flange onto which bears the proximal end of the reset spring.

The drug delivery device may further comprise a last dose protection mechanism for preventing the setting of a dose, which exceeds the amount of liquid left in a cartridge. This has the advantage that the user knows how much will be delivered before starting the dose delivery. It also ensures that dose delivery stops in a controlled manner without the bung entering the neck portion of the cartridge where the diameter is smaller which may result in an underdose. For example, the last dose protection mechanism comprises a nut member interposed between the drive member and the dose setting element (number sleeve) or any other component which rotates during dose setting and dose dispensing. In a preferred embodiment, the dose setting element rotates during dose setting and during dose dispensing, whereas the drive member only rotates during dose dispensing together with the dose setting element. Thus, in this embodiment, the nut member will only move axially during dose setting and will remain stationary with respect to these components during dose dispensing. Preferably, the nut member is threaded to the drive member and splined to the dose setting member. As an alternative, the nut member may be threaded to the dose setting member and may be splined to the drive member. The nut member may be a full nut or a part thereof, e.g. a half nut.

The injection device may comprise at least one clicker mechanism for generating a tactile and/or audible feedback. A feedback may be generated during dose setting (increasing and/or decreasing a dose), dose dispensing and/or at the end of dose dispensing.

The drug delivery device may comprise a cartridge containing a medicament. The term "medicament", as used herein, means a pharmaceutical formulation containing at least one pharmaceutically active compound, wherein in one embodiment the pharmaceutically active compound has a molecular weight up to 1500 Da and/or is a peptide, a protein, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4 (1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4 (1-39), wherein the group -Lys6-NH2 may be bound to the C-terminus of the Exendin-4 derivative;

or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4 (1-39)-(Lys)6-NH2, H-(Lys)6-des Pro36, Pro37, Pro38 [Trp(O2)25, Asp28] Exendin-4(1-39)-(Lys)6-NH2, H-Asn-(Glu)5-des Pro36, Pro37, Pro38 [Trp(O2)25, Asp28] Exendin-4(1-39)-(Lys)6-NH2, H-(Lys)6-des Pro36 [Met(O)14, Asp28] Exendin-4(1-39)-Lys6-NH2, des Met(O)14 Asp28 Pro36, Pro37, Pro38 Exendin-4(1-39)-NH2, H-(Lys)6-desPro36, Pro37, Pro38 [Met(O)14, Asp28] Exendin-4(1-39)-NH2, H-Asn-(Glu)5-des Pro36, Pro37, Pro38 [Met(O)14, Asp28] Exendin-4(1-39)-NH2, des Pro36, Pro37, Pro38 [Met(O)14, Asp28] Exendin-4 (1-39)-(Lys)6-NH2, H-(Lys)6-des Pro36, Pro37, Pro38 [Met(O)14, Asp28] Exendin-4(1-39)-(Lys)6-NH2, H-Asn-(Glu)5 des Pro36, Pro37, Pro38 [Met(O)14, Asp28] Exendin-4(1-39)-(Lys)6-NH2, H-Lys6-des Pro36 [Met(O)14, Trp(O2)25, Asp28] Exendin-4(1-39)-Lys6-NH2, H-des Asp28 Pro36, Pro37, Pro38 [Met(O)14, Trp(O2)25] Exendin-4(1-39)-NH2, H-(Lys)6-des Pro36, Pro37, Pro38 [Met(O)14, Asp28] Exendin-4(1-39)-NH2, H-Asn-(Glu)5-des Pro36, Pro37, Pro38 [Met(O)14, Trp (O2)25, Asp28] Exendin-4(1-39)-NH2, des Pro36, Pro37, Pro38 [Met(O)14, Trp(O2)25, Asp28] Exendin-4(1-39)-(Lys)6-NH2, H-(Lys)6-des Pro36, Pro37, Pro38 [Met(O)14, Trp(O2) 25, Asp28] Exendin-4(S1-S9)-(Lys)6-NH2, H-Asn-(Glu)5-des Pro36, Pro37, Pro38 [Met(O)14, Trp (O2)25, Asp28] Exendin-4(1-39)-(Lys)6-NH2;

or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region (CH) and the variable region (VH). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

BRIEF DESCRIPTION OF THE DRAWINGS

Non-limiting, exemplary embodiments will now be described with reference to the accompanying drawings, in which:

FIG. 2 shows an exploded view of the components of the device of FIG. 1a;

FIG. 3 shows a sectional view of the device of FIG. 1a;

FIG. 4 shows a side view of the gauge element of the device of FIG. 1a;

FIG. 5 shows a detail of the number sleeve of the device of FIG. 1a;

FIG. 6 shows in a sectional view a detail of the device of FIG. 1a;

FIG. 9 shows a detail of the device of FIG. 1a;

FIG. 10 shows a side view of the bias spring of the device of FIG. 1a;

FIGS. 13a-c show in sectional views the sequence of resetting the device of FIG. 1a.

DETAILED DESCRIPTION

Figure 1A:
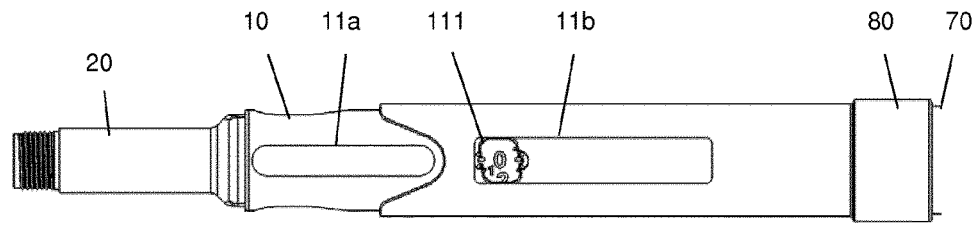
FIG. 1a shows a top view of the drug delivery device in the minimum dose position.
Figure 1B:
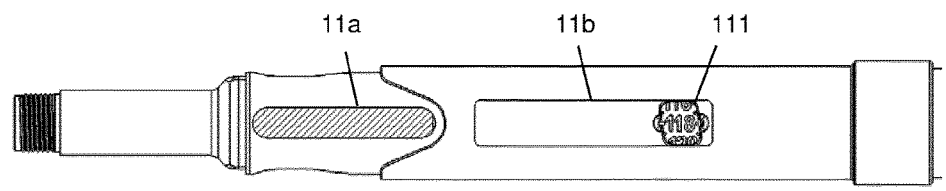
FIG. 1b shows a top view of the drug delivery device of FIG. 1a with a dose of 118 units dialed.
Figure 2:
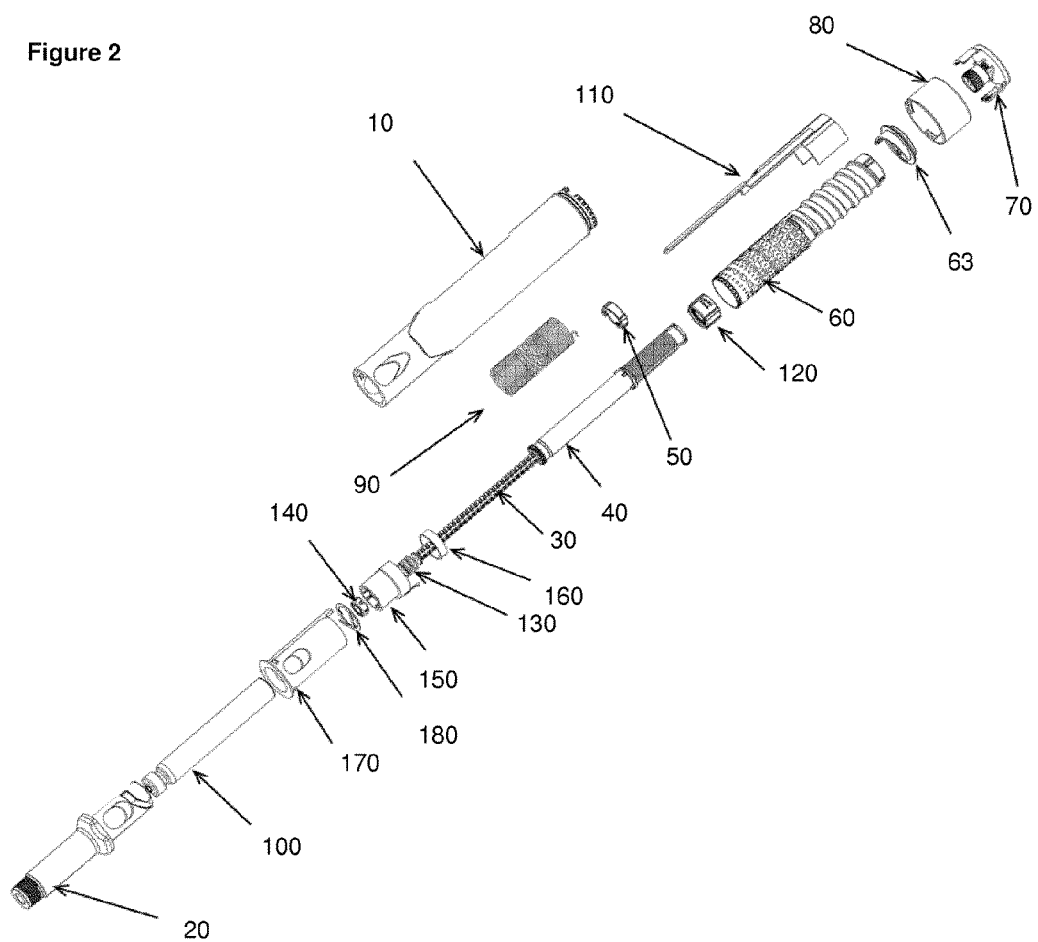

FIG. 1a shows a drug delivery device in the form of an injection pen. The device has a distal end (left end in FIG. 1) and a proximal end (right end in FIG. 1). The component parts of the drug delivery device are shown in FIG. 2. The drug delivery device comprises a body or housing 10, a cartridge holder 20, a lead screw (piston rod) 30, a drive sleeve 40, a nut 50, a dose setting element which is a dose indicator (number sleeve) 60, a button 70, a dial grip or dose selector 80, a torsion spring 90, a cartridge 100, a gauge element 110, a clutch element 120, a clutch spring 130, a bearing 140, a reset element 150, a reset spring 160, an inner body 170 and a bias spring 180. A needle arrangement (not shown) with a needle hub and a needle cover may be provided as additional components, which can be exchanged as explained above. All components are located concentrically about a common principal axis I of the mechanism which is shown in FIG. 3.

The housing 10 or body is a generally tubular element having a proximal end with an enlarged diameter. An inner body 170 is fixed to and partially received in the housing 10. The housing 10 provides location for the liquid medication cartridge 100 and cartridge holder 20, windows 11a, 11b for viewing the dose number on the dose indicator 60 and the gauge element 110, and a feature on its external surface, e.g. a circumferential groove, to axially retain the dose selector 80. The housing 10 further has at least one internal, axially orientated slot or the like for axially guiding the gauge element 110.

The cartridge holder 20 is located at the distal end of housing 10 and attached thereto in a releasable manner. The cartridge holder may be a transparent or translucent component which is tubular to receive cartridge 100. The distal end of cartridge holder 20 may be provided with means for attaching a needle arrangement. A removable cap (not shown) may be provided to fit over the cartridge holder 20 and may be retained via clip features on the housing 10. The cartridge holder 20 contains the replaceable cartridge 100 and acts to axially align the reset plate 150 spline teeth 151 with the drive sleeve 40 spline teeth 41. When the cartridge holder 20 is removed, the trigger spring 130 and/or the reset spring 160 force the reset element 150 axially in a distal direction, removing the alignment of the spline teeth 151 to the drive sleeve 40 thereby allowing the device to be reset.

The piston rod 30 is an elongate lead screw element with an outer thread 31 and at least one axially extending spline or rib. The piston rod 30 is rotationally constrained to the drive sleeve 40 via this splined interface. When rotated, the piston rod 30 is forced to move axially relative to the housing 10, through a threaded interface 31, 152 with the reset element 150. The bearing 140 is attached to the distal end of the piston rod 30, e.g. by a snap connection.

The drive sleeve 40 is a tubular member surrounding the piston rod 30 and being at least in part received within the dose setting element 60. The drive sleeve 40 extends from the interface 42, 121 with the dose setting element 60 (via the clutch plate 120) down to a splined tooth interface 41, 151 (FIG. 6) with the reset element 150. This provides a rotational constraint to the drive sleeve 40 during dose setting. When the button 70 is pressed, these spline teeth 41, 151 are disengaged allowing the drive sleeve 40 to rotate under the action of the drive spring 90, dispensing the set dose. Pressing the button 70 also engages an additional spline clutch 43, 61 (FIG. 7a) between the drive sleeve 40 and dose setting element 60. This ensures there can be no relative rotation between the drive sleeve 40 and dose setting element 60 during dispense. The drive sleeve has near its distal end a seat for trigger spring 130. A threaded portion 44 engages last dose nut 50.

The last dose nut 50 is located between the dose setting element 60 and the drive sleeve 40. It is rotationally constrained to the dose setting element 60, via a splined interface. It moves along a helical path relative to the drive sleeve 40, via a threaded interface 44, when relative rotation occurs between the dose setting element 60 and drive sleeve 40, i.e. during dialling and resetting only.

The dose setting element 60 is a tubular number sleeve which is constrained at its proximal end to the dial grip 80 and to the housing 10 at its distal end to allow rotation but not axial translation. The dose setting element 60 is marked with a sequence of numbers, which are visible through opening 111 (FIG. 4) in the gauge element 110 and the slot-like window 11b in the housing 10, to denote the dialled dose of medicament. On the inner surface of the dose setting element 60 splines 61 are provided for engaging corresponding splines 43 on the outer surface of the drive sleeve 40 depending on the relative axial position of the drive sleeve and the dose setting element. The dose setting element 60 is provided with a threaded portion 62 engaging gauge element 110. Splines 63 are provided at or near the proximal end of dose setting element 60 on a separate component part permanently fixed to the dose setting element 60. This separate part could be made as an integral part with the dose setting element. There are further spline features 64 at or near the distal end of dose setting element 60 for engaging arm 153 of reset element 150.

The button 70 is splined to the dose setting element 60 when in the dose dialling condition. This spline interface 63, 71 is disconnected when the button 70 is pressed to trigger a dispense. When depressed, the button 70 is rotationally constrained to the housing 10 via a splined engagement 72, 12.

The dose selector 80 is radially constrained to the housing 10 and rotationally constrained to the button 70.

The drive spring 90 is attached at one end to the housing 10 and at the other end to the dose setting element 60. The drive spring 90 is pre-wound upon assembly, such that it applies a torque to the dose setting element 60 when the mechanism is at zero count dialled. The action of rotating the dial grip 80, to set a dose, rotates the dose setting element 60 relative to the housing 10, and charges the drive spring 90.

The gauge element 110 is constrained to prevent rotation but allow translation relative to the housing 10 via a splined interface. The gauge element 110 has helical features 112 on its inner surface which engage with the helical thread formed in the threaded portion 62 of dose setting element 60 such that rotation of the dose setting element 60 causes axial translation of the gauge element 110. As shown in FIGS. 4 and 5, these helical features 112 on the gauge element 110 also create stop abutments against the ends of the helical thread in the dose setting element 60 to limit the minimum and maximum dose that can be set.

The clutch plate 120 is splined to the dose setting element 60. It is also coupled to the drive sleeve 40 via a ratchet interface 42, 121, which occurs on an axial abutment. The ratchet interface 42, 121 provides a detented position between the dose setting element 60 and drive sleeve 40 corresponding to each dose increment, and engages different ramped tooth angles during clockwise and anti-clockwise relative rotation.

The relative axial position of the drive sleeve 40, clutch plate 120 and button 70 are influenced by the action of the trigger spring 130, which applies a biasing force on the drive sleeve 40 in the proximal direction. In the at rest position, this ensures that the button 70 splines are engaged with the dose setting element 60 and that the drive sleeve 40 teeth are engaged with the reset element 150.

The bearing 140 is axially constrained to the piston rod 30 and acts on the bung within the liquid medicament cartridge 100.

Figure 14A:
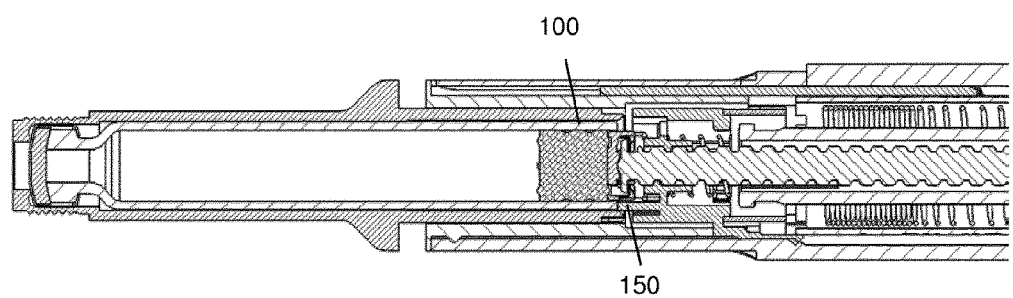
FIGS. 14a, b show in sectional views the sequence of resetting the device of an alternative embodiment.
Figure 14B:
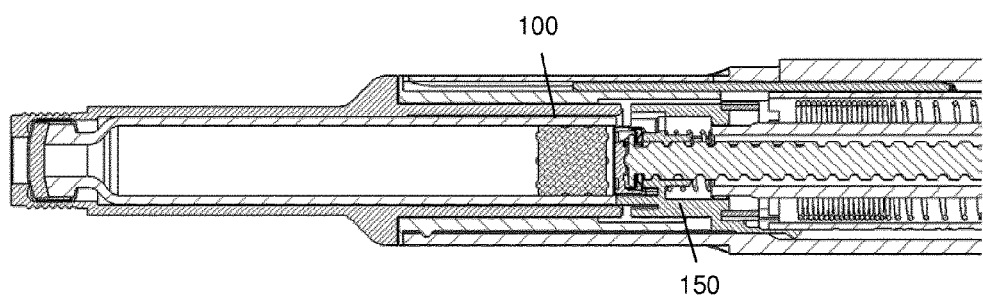

The reset element 150 is rotationally splined to the housing 10 and biased in a distal direction by the reset spring 160. It also houses the bias spring 180 which acts axially upon the cartridge 100. Further trigger spring 130 is supported by reset element 150. The reset element 150 contains spline teeth 151 that prevent rotation of the drive sleeve 40 during dialling of the device. As an alternative, the reset element 150 could also bias the cartridge 100 directly, as shown in the alternative embodiment of FIGS. 14a, 14b. An inner thread 152 engages outer thread 31 of the piston rod 30. Further, reset element 150 is provided with at least one flexible arm 153 extending in the proximal direction. Arm 153 is guided in abutment with an inner housing surface having a step as shown in FIG. 6 such that axial movement of the reset element 150 in the distal direction deflects arm 153 radially inwards to rotationally lock dose setting element 60 to reset element 150.

The inner body 170 is rigidly fixed to the housing 10, and provides locking features for the cartridge holder 20. The housing 10 and the inner body 170 can be functionally treated as one component.

Figure 8A:
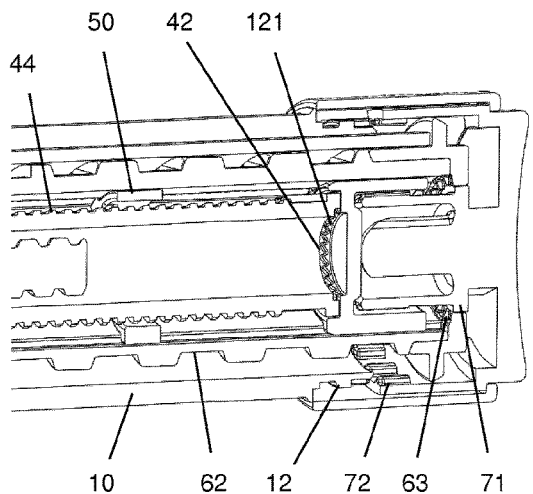
FIGS. 8a, b show details of FIGS. 7a, b.
Figure 7A:
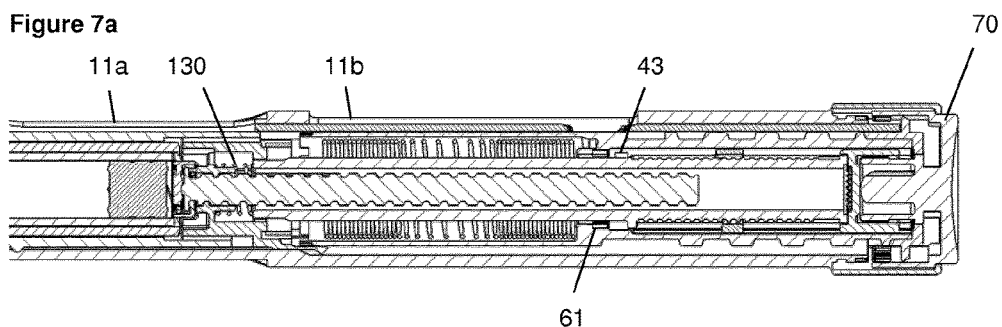
FIGS. 7a, b show in a sectional view the device of FIG. 1a in the dose setting mode and in the dose dispensing mode.
Figure 7B:
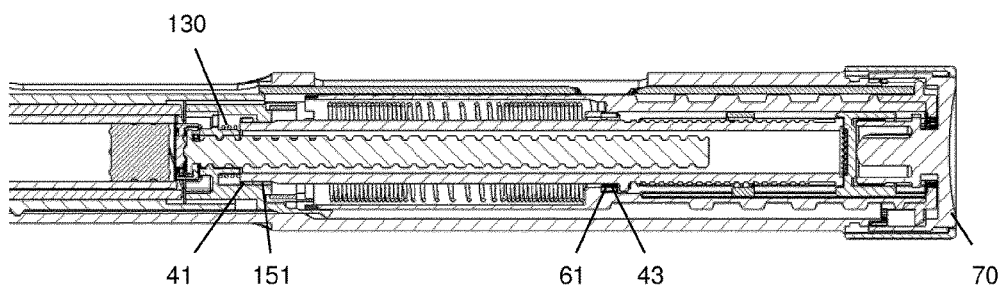

The main functions of the device are now described in more detail: With the device in the at rest condition, the dose setting element 60 is positioned against its zero dose abutment with the gauge element 110 and the button 70 is not depressed (FIGS. 7a, 8a). Dose marking '0' on the dose setting element 60 is visible through the window of the housing 10 and gauge element 110 as shown in FIG. 1a. The drive spring 90, which has a number of pre-wound turns applied to it during assembly of the device, applies a torque to the dose setting element 60 and is prevented from rotating by the zero dose abutment. It is also possible to back-wind the mechanism slightly due to an offset between the zero dose stop and the angular offset of spline teeth 41 of the drive sleeve 40. This has the effect of preventing possible weepage when a dose is dialled and the zero dose abutment is disengaged.

The user selects a variable dose of liquid medicament by rotating the dial grip 80 clockwise, which generates an identical rotation in the dose setting element 60. Rotation of the dose setting element 60 causes charging of the drive spring 90, increasing the energy stored within it. As the dose setting element 60 rotates, the gauge element 110 translates axially due to its threaded engagement thereby showing the value of the dialled dose. The gauge element 110 has flanges (opaque surfaces) either side of the window 111 area which cover the numbers printed on the dose setting element 60 adjacent to the dialled dose to ensure only the set dose number is made visible to the user. One specific element of this mechanism is inclusion of a visual feedback feature in addition to the discrete dose number display typical on devices of this type. The distal end of the gauge element 110 creates a sliding scale (although this could be formed using a separate component engaged with the dose setting element 60 on a different helical track if desired) through the window 11a in the housing 10. As a dose is set by the user the gauge element 110 translates axially, the distance moved proportional to the magnitude of the dose set. This feature gives clear feedback to the user regarding the approximate size of the dose set. The dispense speed of an auto-injector mechanism may be higher than for a manual injector device, so it may not be possible to read the numerical dose display during dispense. The gauge element 110 feature provides feedback to the user during dispense regarding dispense progress without the need to read the dose number itself. This additional visual feedback provided by the gauge element 110 can be seen by comparing FIGS. 1a and 1b with window 11a either being shielded internally by the gauge element (FIG. 1a) or revealing a contrasting surface by axial movement of the gauge element 110 (FIG. 1b). In addition, window 111 moves axially within window 11b which gives a further indication of the set dose.

The gauge element 110 display may be formed by an opaque sliding element revealing a contrasting coloured component underneath. Alternatively, the concealed component may be printed with coarse (occasional) dose numbers or other indices to provide more precise resolution. In addition, the gauge element 110 display simulates a syringe action during dose set and dispense.

The drive sleeve 40 is prevented from rotating as the dose is set and the dose setting element 60 rotated due to the engagement of its splined teeth 41 with teeth 151 of the reset element 150. Relative rotation must therefore occur between the clutch plate 120 and drive sleeve 40 via the ratchet interface 42, 121. The user torque required to rotate the dial grip 80 is a sum of the torque required to wind up the drive spring 90, and the torque required to overhaul the ratchet feature 42, 121. The trigger spring 130 is designed to provide an axial force to the ratchet feature 42, 121 and to bias the clutch plate 120 onto the drive sleeve 40. This axial load acts to maintain the ratchet teeth engagement of the clutch plate 120 and drive sleeve 40. The torque required to overhaul the ratchet 42, 121 in the dose set direction is a function of the axial load applied by the trigger spring 130, the clockwise ramp angle of the ratchet 42, 121, the friction coefficient between the mating surfaces and the mean radius of the ratchet features.

As the user rotates the dial grip 80 sufficiently to increment the mechanism by 1 increment, the dose setting element 60 rotates relative to the drive sleeve 40 by 1 ratchet tooth. At this point the ratchet teeth re-engage into the next detented position. An audible click is generated by the ratchet re-engagement, and tactile feedback is given by the change in torque input required.

Relative rotation of the dose setting element 60 and the drive sleeve 40 also causes the last dose nut 50 to travel along its threaded path, towards its last dose abutment on the drive sleeve 40.

With no user torque applied to the dial grip 80, the dose setting element 60 is now prevented from rotating back under the action of the drive spring 90, solely by the ratchet 42, 121 engagement between the clutch plate 120 and drive sleeve 40. The torque necessary to overhaul the ratchet 42, 121 in the anti-clockwise direction is a function of the axial load applied by the trigger spring 130, the anti-clockwise ramp angle of the ratchet, the friction coefficient between the mating surfaces and the mean radius of the ratchet features. The torque necessary to overhaul the ratchet must be greater than the torque applied to the dose setting element 60 (and hence clutch plate 120) by the drive spring 90. The ratchet ramp angle is therefore increased in the anti-clockwise direction to ensure this is the case whilst ensuring the dial-up torque is acceptably low.

The user may now choose to increase the selected dose by continuing to rotate the dial grip 80 in the clockwise direction. FIG. 1*b* shows the device with a dose of 118 units dialled. The process of overhauling the ratchet interfaces 42, 121 between the dose setting element 60 and drive sleeve 40 is repeated for each dose increment. Additional energy is stored within the drive spring 90 for each dose increment and audible and tactile feedback is provided for each increment dialled by the re-engagement of the ratchet teeth. The torque required to rotate the dial grip 80 increases as the torque required to wind up the drive spring 90 increases. The torque required to overhaul the ratchet in the anti-clockwise direction must therefore be greater than the torque applied to the dose setting element 60 by the drive spring 90 when the maximum dose has been reached.

If the user continues to increase the selected dose until the maximum dose limit is reached, the dose setting element 60 engages with its maximum dose abutment on the gauge element 110. This prevents further rotation of the dose setting element 60, clutch plate 120 and dial grip 80.

Depending on how many increments have already been delivered by the mechanism, during selection of a dose, the last dose nut 50 may contact its last dose abutment with the drive sleeve 40. The abutment prevents further relative rotation between the dose setting element 60 and the drive sleeve 40, and therefore limits the dose that can be selected. The position of the last dose nut 50 is determined by the total relative rotation between the dose setting element 60 and drive sleeve 40 that has accumulated each time the user has set a dose.

With the mechanism in a state in which a dose has been selected, the user is able to deselect any number of increments from this dose. Deselecting a dose (dose correction) is achieved by the user rotating the dial grip 80 anti-clockwise. The torque applied to the dial grip 80 by the user is sufficient, when combined with the torque applied by the drive spring 90, to overhaul the ratchet 42, 121 between the clutch plate 120 and drive sleeve 40 in the anti-clockwise direction. When the ratchet 42, 121 is overhauled, anti-clockwise rotation occurs in the dose setting element 60 (via the clutch plate 120), which returns the dose setting element 60 towards the zero dose position, and unwinds the drive spring 90. The relative rotation between the dose setting element 60 and drive sleeve 40 causes the last dose nut 50 to return along its helical path, away from the last dose abutment.

Figure 8B:
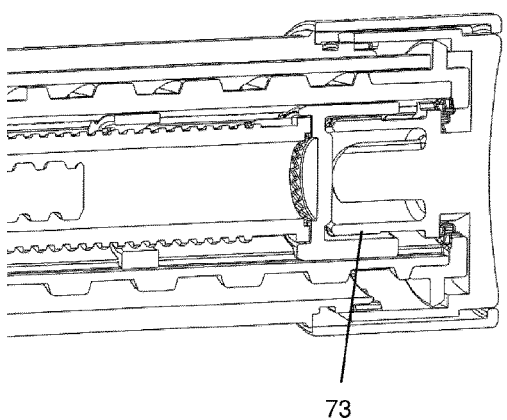

With the mechanism in a state in which a dose has been selected, the user is able to activate the mechanism to commence delivery of a dose. Delivery of a dose is initiated by the user depressing the button 70 axially. When the button 70 is depressed, splines 63, 71 between the button 70 and dose setting element 60 are disengaged, rotationally disconnecting the button 70 and dial grip 80 from the delivery mechanism. Splines 72 on the button 70 also engage with splines 12 on the housing 10 so that the dial grip 80 and button 70 do not rotate during dispense (FIGS. 8*a*, 8*b*). The button 70 acts on the drive sleeve 40, via the clutch plate 120, which travels axially and disconnects the splined engagement 41, 151 with the reset element 150. The drive sleeve 40 can now rotate and is driven by the drive spring 90 via the dose setting element 60, and clutch plate 120. Rotation of the drive sleeve 40 causes the piston rod 30 to rotate due to their splined engagement, and the piston rod 30 then advances due to its threaded engagement 31, 152 to the reset element 150. The dose setting element 60 rotation also causes the gauge element 110 to traverse axially back to its zero position whereby the zero dose abutment stops the mechanism.

During dispense the additional splined interface 43, 61 between the drive sleeve 40 and dose setting element 60 is engaged to prevent free rotation of the dose setting element 60 if the button 70 force is removed part way through a dispense, where the clutch plate 120 to drive sleeve 40 ratchet may be momentarily unloaded before the drive sleeve 40 re-establishes its rotational engagement with the splines of reset element 150.

Figure 9:
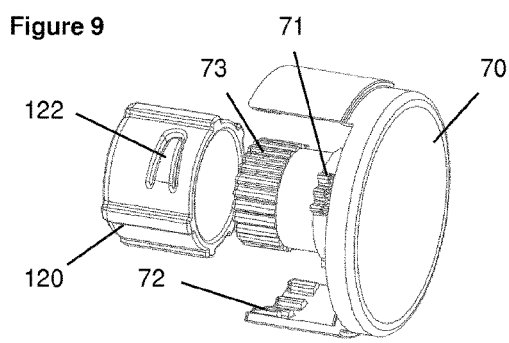

Tactile feedback during dose dispense is provided via a compliant cantilever clicker arm 122 integrated into the cylindrical side wall of the clutch plate 120 (FIG. 9). This clicker arm 122 interfaces radially with ratchet features in the form of clicker teeth 73 on the button 70. During dispense, as the dose setting element 60 and hence clutch plate 120 rotate and the button 70 is rotationally coupled to the housing 10, the ratchet features 73 interact with the clicker arm 122 to produce an audible click with each dose count delivered.

Delivery of a dose continues via the mechanical interactions described above while the user continues to depress the button 70. If the user releases the button 70, the trigger spring 130 returns the button 70 to its at rest position via the drive sleeve 40 and clutch plate 120, the drive sleeve 40 becomes rotationally constrained and delivery of a dose is halted.

During delivery of a dose, the drive sleeve 40 and dose setting element 60 rotate together, so that no relative motion in the last dose nut 50 occurs. The last dose nut 50 therefore travels axially along the drive sleeve 40 only during dialling.

Once the delivery of a dose is stopped by the dose setting element 60 returning to the zero dose abutment, the user may release the button 70, which will re-engage the drive sleeve 40 spline teeth with the reset element 150. The mechanism is now returned to the at rest condition.

Figure 10:
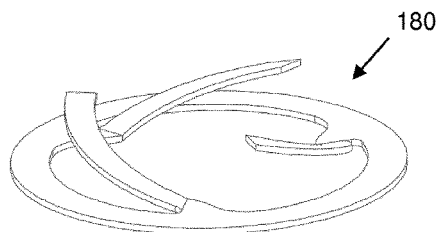

The mechanism also contains a bias spring 180 (FIG. 10) which acts on the rear rim of the cartridge 100 to bias it in a distal direction. This aids dose accuracy as it ensures the cartridge is always biased distally, removing the effect of tolerances and the possibility of the cartridge 100 moving proximally when a needle is fitted to the device. In the embodiment shown, the bias spring 180 consists of a simple sheet metal component, but it may equally be any spring means.

It is possible to angle the spline teeth 41, 151 on either the drive sleeve 40 or reset element 150 so that when the button 70 is released the re-engagement of the spline teeth fractionally backwinds the drive sleeve 40 thereby removing the engagement of the dose setting element 60 to the gauge element 110 zero dose stop abutment. This compensates for the effect of clearances in the mechanism, for example due to tolerances, which could otherwise lead to slight advancement of the piston rod 30 and medicament dispense when the device is dialled for the subsequent dose due to the dose setting element 60 zero dose stop no longer restraining (controlling) the mechanism and instead the restraint (control) returning to the splines between the drive sleeve 40 and housing 10.

Figure 11:
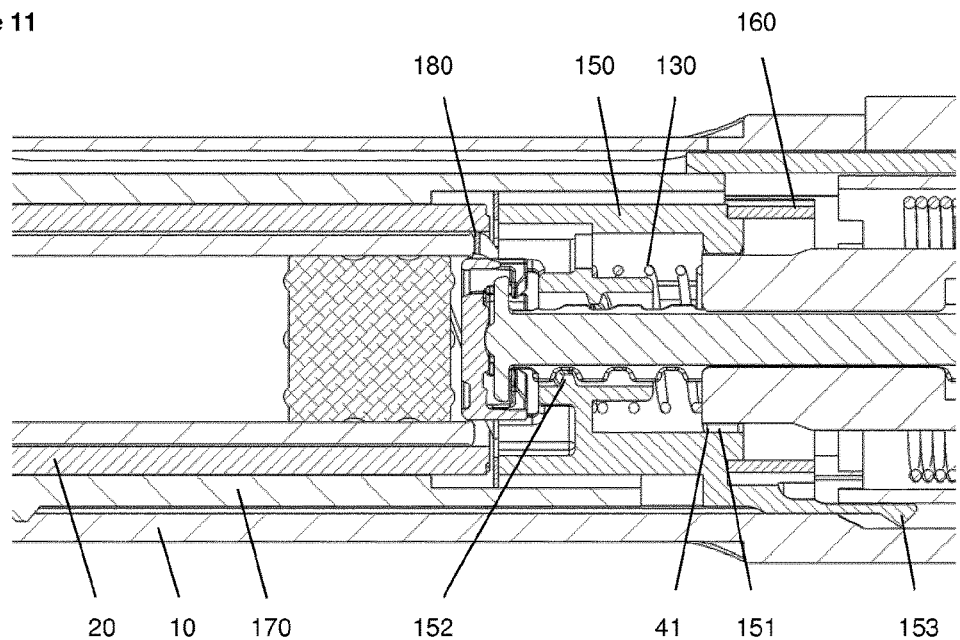
FIG. 11 shows a detail of the device of FIG. 1a with the cartridge holder attached.
Figure 12:
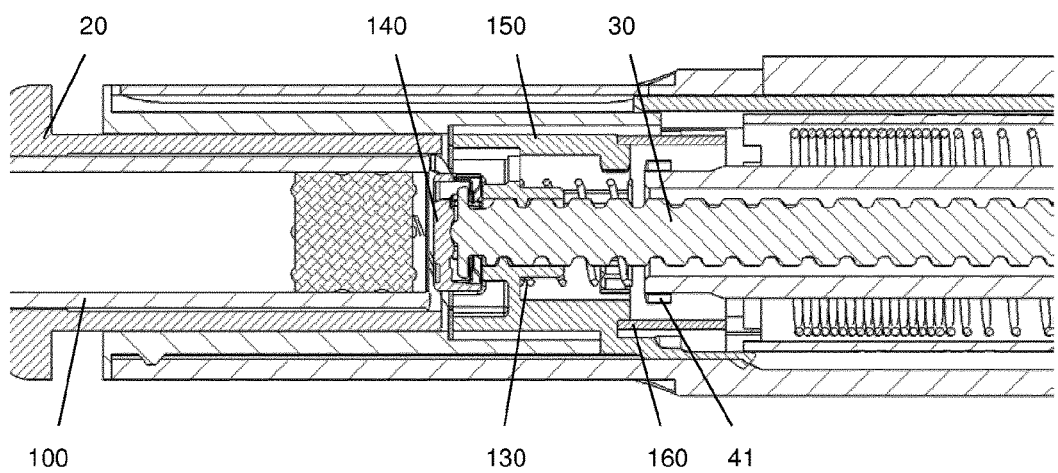
FIG. 12 shows a detail of the device of FIG. 1a with the cartridge holder partly detached.

To reset the mechanism, the user first unscrews the cartridge holder 20, which allows the reset spring 160 to move the reset element 150 axially in a distal direction. This axial travel is sufficient to disconnect the splines 151 from the drive sleeve 40. It also removes compression from the trigger spring 130. Simultaneously, the flexible arm 153 on the reset element 150 is forced into engagement with spline features 64 on the dose setting element 60, locking it against rotation. This ensures that if a dose has been dialled, the drive spring 90 cannot return the dose setting element 60 to its zero position during the reset operation. A comparison of FIGS. 11 and 12 shows how the reset element 150 is moved axially when the cartridge holder 20 is removed due to the force exerted by the reset spring 160.

The user can then fit a new cartridge 100 into the cartridge holder 20, and the bearing 140 and piston rod 30 be pushed back into the mechanism. As the piston rod 30 is returned into the mechanism, a rotation in the piston rod 30 is generated due to the thread interface 31, 152 with the reset element 150. This piston rod 30 rotation causes the drive sleeve 40 to rotate due to their spline interface, which acts to backwind the last dose nut 50 towards its start position. Since the axial force is removed from the trigger spring 130, the ratchet feature 121 of the clutch plate 120 generates negligible torque loss and does not transfer significant torque into the dose setting element 60.

Figure 13A:
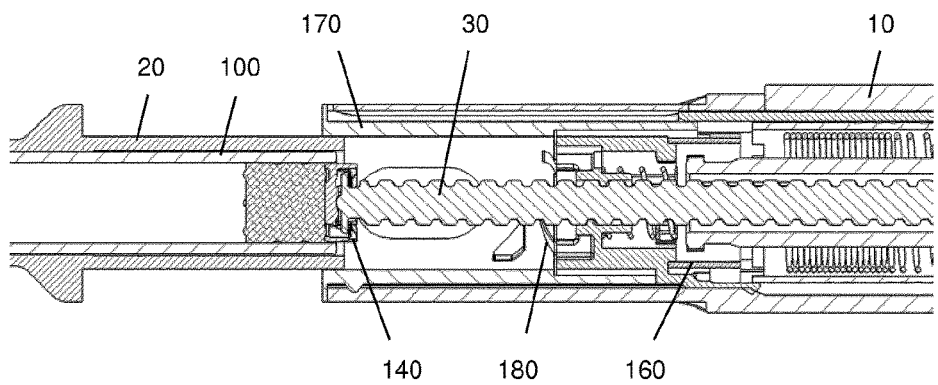
Figure 13B:
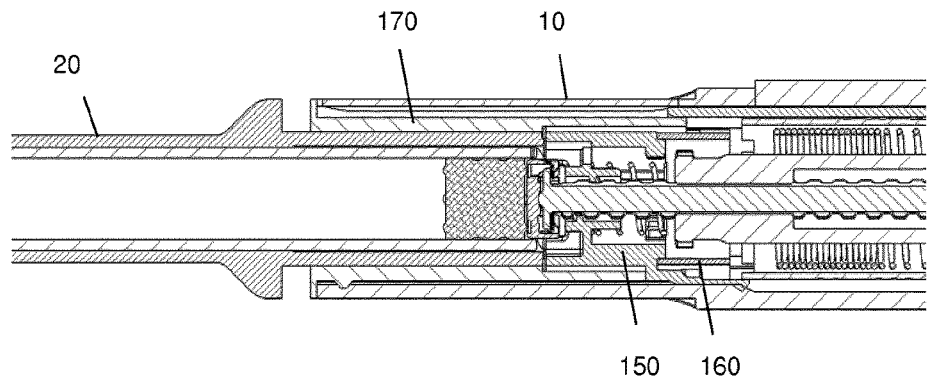
Figure 13C:
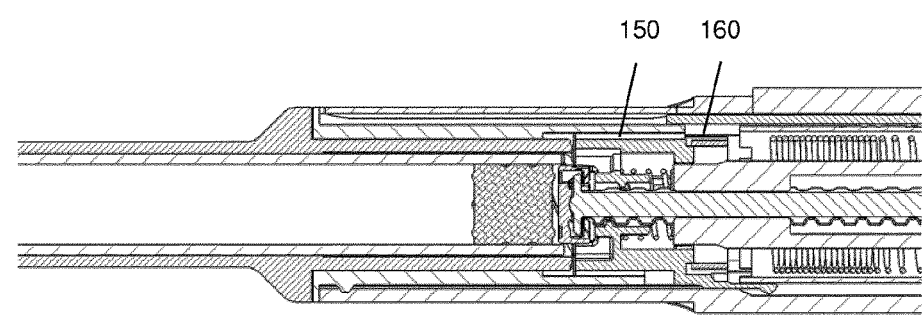

During resetting of the mechanism, the force applied to the bearing 140 is less than the force exerted on the reset element 150 by the reset spring 160, and therefore the reset element 150 does not move axially in a proximal direction which would otherwise cause the drive sleeve 40 splines to re-engage, locking the mechanism and preventing further reset. Towards the end of reset, the cartridge holder 20 contacts the reset element 150, and acts to move the reset element 150 in a proximal direction, reengaging it with the drive sleeve 40 splines. During this final stage of reset, the reset element 150 and piston rod 30 move proximally without rotation at the same rate as the cartridge 100. Therefore no axial compression is generated in the cartridge bung. FIGS. 13a to 13c show the sequence of resetting and attaching the cartridge holder 20, wherein FIG. 13a shows the start of reset (reset element 150 is biased distally), FIG. 13b shows a position approaching full reset with the cartridge holder abutment contacting reset element 150 and FIG. 13c shows that the cartridge holder forces the reset element 150 in a proximal direction, re-engaging the splines 41, 151 to the drive sleeve 40.

As an alternative it is possible to achieve cartridge biasing directly from the reset element 150 without the use of a separate bias spring 180. In this embodiment shown in FIGS. 14a, 14b, during the final stages of reset the cartridge glass contacts the reset element 150 causing the reset element 150 to travel proximally and engage with the drive sleeve 40 splines. In the event that the cartridge holder 20 is fitted without a cartridge 100, there are two options available that can be accommodated within the design: The reset element 150 will not travel back to its nominal position and therefore the dose setting element 60 will remain locked and the user will not be able to dial a dose. This also acts to prevent the user from dispensing a dose when no cartridge is installed, which may damage the autoinjector mechanism as it returns to its zero position at high speed and under no load. Alternatively, the reset element 150 contacts the cartridge holder 20, and is moved in a proximal direction by an amount sufficient to engage the drive sleeve 40 splines.

| Reference Numerals: | |
|---|---|
| 10 | housing |
| 11a, b | opening (window, aperture) |
| 12 | spline |
| 20 | cartridge holder |
| 30 | piston rod (lead screw) |
| 31 | outer thread |
| 40 | drive sleeve |
| 41 | teeth |
| 42 | ratchet teeth |
| 43 | spline |
| 44 | threaded portion |
| 50 | nut (last dose nut) |
| 60 | dose setting element (dose indicator, number sleeve) |
| 61 | spline |
| 62 | threaded portion |
| 63 | spline |
| 64 | spline |
| 70 | button |
| 71 | spline |
| 72 | spline |
| 73 | clicker teeth |
| 80 | dose selector |
| 90 | torsion spring |
| 100 | cartridge |
| 110 | gauge element |
| 111 | opening (window, aperture) |
| 112 | helical features |
| 120 | clutch plate (clutch element) |
| 121 | ratchet teeth |
| 122 | clicker arm |
| 130 | clutch spring (trigger spring) |
| 140 | bearing |
| 150 | reset plate (reset element) |
| 151 | clutch teeth |
| 152 | inner thread |

-continued

| Reference Numerals: | |
|---|---|
| 153 | arm |
| 160 | cartridge holder spring (reset spring) |
| 170 | inner body |
| 180 | bias spring |
| 1 | longitudinal axis |

The invention claimed is:

1. A drug delivery device for selecting and dispensing a number of user variable doses of a medicament, the drug delivery device comprising:
   a housing;
   a dose setting element rotatable relative to the housing during dose setting and dose dispensing;
   a drive member coupled to the dose setting element via a clutch;
   a piston rod coupled to the housing and to the drive member;
   a cartridge holder removably attached to the housing and a reset element, which is permanently rotationally constrained to the housing and rotationally constrained to the drive member during dose setting; and
   at least one spring acting on the reset element,
   wherein if the cartridge holder is detached from the housing, the reset element is axially moved relative to the housing into a position in which the drive member is allowed to rotate relative to the housing, and
   wherein the drive member is axially movable relative to the housing between a dose setting position and a dose dispensing position, wherein in the dose setting position, if the cartridge holder is attached to the housing, the drive member is rotationally constrained to the housing via the reset element, and wherein in the dose dispensing position, if the cartridge holder is attached to the housing, the drive member is rotatable relative to the reset element and the housing.

2. The drug delivery device according to claim 1, wherein, if the cartridge holder is attached to the housing, the cartridge holder holds the reset element against a bias of the at least one spring into a position in which the drive member is releasably rotationally constrained to the housing.

3. The drug delivery device according to claim 1, wherein the reset element comprises clutch teeth and the drive member comprises corresponding clutch teeth for releasably rotationally constraining the reset element and the drive member depending on relative axial positions of the reset element and the drive member.

4. The drug delivery device according to claim 1, wherein the clutch between the drive member and the dose setting element is a slipping clutch comprising first clutch teeth on the drive member and second clutch teeth on the dose setting element.

5. The drug delivery device according to claim 4, wherein the at least one spring biases the drive member into abutment with the dose setting element.

6. The drug delivery device according to claim 1, wherein the clutch between the drive member and the dose setting element is a slipping clutch comprising first clutch teeth on the drive member and second clutch teeth on a clutch plate, which is permanently rotationally constrained to the dose setting element.

7. The drug delivery device of claim 6, wherein the at least one spring biases the drive member into abutment with the clutch plate.

8. The drug delivery device according to claim 1, further comprising a clutch which is decoupled if the cartridge holder is attached to the housing and which is coupled if the cartridge holder is detached from the housing, wherein the clutch rotationally couples the dose setting element and the reset element.

9. The drug delivery device according to claim 8, wherein the clutch comprises at least one flexible arm which is guided into engagement with the dose setting element upon axial movement of the reset element into a resetting position.

10. The drug delivery device according to claim 1, further comprising a bias spring interposed between the reset element and a cartridge retained in the cartridge holder.

11. The drug delivery device according to claim 1, wherein the piston rod comprises an outer thread engaging an inner thread of the reset element.

12. The drug delivery device according to claim 1, further comprising a drive spring interposed between the housing and the dose setting element.

13. The drug delivery device of claim 12, wherein the drive spring is a torsion spring.

14. The drug delivery device according to claim 1, further comprising a gauge element radially interposed between the housing and the dose setting element, wherein the gauge element is axially movable relative to the housing and in threaded engagement with the dose setting element.

15. The drug delivery device according to claim 14, wherein the housing comprises at least one aperture, wherein the gauge element comprises at least one aperture, wherein the dose setting element comprises markings on its outer surface, and wherein at least one of the markings is visible through the aperture in the gauge element and the aperture in the housing during dose setting and dose dispensing.

16. The drug delivery device according to claim 14, wherein the gauge element comprises a minimum dose rotational stop and a maximum dose rotational stop and the dose setting element comprises a minimum dose rotational counter stop and a maximum dose rotational counter stop.

17. The drug delivery device according to claim 1, comprising a cartridge containing a medicament.

18. The drug delivery device of claim 17, wherein the medicament comprises a pharmaceutically active compound.

19. The drug delivery device of claim 17, wherein the cartridge is disposed in the cartridge holder.

* * * * *